(12) United States Patent
Rehfinger et al.

(10) Patent No.: US 6,300,497 B1
(45) Date of Patent: Oct. 9, 2001

(54) METHOD FOR SEPARATING AN AZEPINE DERIVATIVE FROM A MIXTURE CONTAINING AN AMINE AND AN AZEPINE DERIVATIVE

(76) Inventors: Alwin Rehfinger, Rosenstr.10, 67112 Mutterstadt; Hermann Luyken, Brüsseler Ring 34, 67069 Ludwigshafen, both of (DE)

( * ) Notice: Subject to any disclaimer, the term of this patent is extended or adjusted under 35 U.S.C. 154(b) by 0 days.

(21) Appl. No.: 09/623,699

(22) PCT Filed: Mar. 18, 1999

(86) PCT No.: PCT/EP99/01786

§ 371 Date: Sep. 7, 2000

§ 102(e) Date: Sep. 7, 2000

(87) PCT Pub. No.: WO99/48872

PCT Pub. Date: Sep. 30, 1999

(30) Foreign Application Priority Data

Mar. 20, 1998 (DE) ............................................ 198 12 427

(51) Int. Cl.⁷ ...................... C07D 223/04; C07D 223/12
(52) U.S. Cl. .......................................... 540/605; 540/612
(58) Field of Search ..................................... 540/605, 612

(56) References Cited

U.S. PATENT DOCUMENTS

| 2,208,598 | 7/1940 | Rigby | 260/464 |
|---|---|---|---|
| 2,762,835 | 9/1956 | Swerdloff | 260/465.5 |
| 3,696,153 | 10/1972 | Kershaw . | |
| 4,601,859 | 7/1986 | Galle | 558/459 |

FOREIGN PATENT DOCUMENTS

| 848 654 | 7/1949 | (DE) . |
|---|---|---|
| 42 35 466 | 4/1994 | (DE) . |
| 195 00222 | 7/1996 | (DE) . |
| 195 48289 | 6/1997 | (DE) . |
| 893 709 | 4/1962 | (GB) . |
| 1 041 442 | 9/1966 | (GB) . |
| 1 238 351 | 7/1971 | (GB) . |
| 92/21650 | 12/1992 | (WO) . |
| 93/14064 | 7/1993 | (WO) . |
| 93/16984 | 9/1993 | (WO) . |
| 96/20931 | 7/1996 | (WO) . |
| 98/34900 | 8/1998 | (WO) . |

OTHER PUBLICATIONS

Ind.Org.Che.Weissermel et al., 1988, 266.

ChemAbst,76,No. 5, 24676, XP002117446.

Primary Examiner—Bruck Kifle

(57) ABSTRACT

A process for distillative removal of part or all of an azepine derivative (III) selected from the group consisting of aminohexylideneimine, tetrahydroazepine, hexylhexahydroazepine and aminohexylhexahydroazepine from a mixture (II) comprising an azepine derivative (III) and an amine (I) comprises conducting the distillation with an overhead temperature of from 160 to 250° C.

2 Claims, No Drawings

METHOD FOR SEPARATING AN AZEPINE DERIVATIVE FROM A MIXTURE CONTAINING AN AMINE AND AN AZEPINE DERIVATIVE

The present invention relates to a process for distillative removal of part or all of an azepine derivative (III) selected from the group consisting of tetrahydroazepine, 2-aminoazepan, N-(2-azepano)-1,6-diaminohexane and N-(2-azepano)-6-aminocapronitrile from a mixture (II) comprising an azepine derivative (III) and an amine (I) selected from the group consisting of 6-aminocapronitrile and hexamethylenediamine, which comprises conducting the distillation with an overhead temperature of from 160 to 250° C.

Mixtures comprising an amine and an azepine derivative are customarily obtained in the hydrogenation of nitriles to amines.

The complete hydrogenation of adiponitrile (ADN) to hexamethylenediamine (HMD), and also the partial hydrogenation with coproduction of HMD and 6-aminocapronitrile (ACN), in the presence of a catalyst based on a metal such as nickel, cobalt, iron, rhodium or ruthenium is commonly known, for example from: K. Weissermel, H.-J. Arpe, Industrielle Organische Chemie, 3rd edition, VCH Verlagsgesellschaft mbH, Weinheim, 1988, page 266, U.S. Pat. Nos. 4,601,859, 2,762,835, 2,208, 598, DE-A 848 654, DE-A 954 416, DE-A 42 35 466, U.S. Pat. No. 3,696,153, DE-A 19500222, WO 92/21650 and German application 19548289.1.

By-products formed include azepine derivatives such as N-(2-azepano)-1,6-diaminohexane and N-(2-azepano)-6-aminocapronitrile, especially 2-aminoazepan and tetrahydroazepine.

These azepine derivatives, which, because of their color and deleterious effect on product properties, constitute undesirable impurities in the amines, which are customarily used for manufacturing fibers, are difficult to separate from the amines.

For instance, GB-A-893 709 discloses installing a delay time vessel in the reflux line of a distillation column used for purifying hexamethylenediamine.

GB-A-1 238 351 describes the removal of HMD from mixtures comprising HMD and azepine derivatives, by addition of alkali metal hydroxide mixtures.

GB-A-1 041 442 discloses passing carbon dioxide into a distillation column used for removing HMD from mixtures comprising HMD and azepine derivatives, during the distillation.

Disadvantages with the processes mentioned are the use of large vessels, which makes for reduced control of the distillation columns, and the formation of solids, which can lead to blockages.

It is an object of the present invention to provide a process for removing an azepine derivative from mixtures comprising an amine and an azepine derivative in a technically simple and economical manner.

We have found that this object is achieved by the process defined at the beginning.

Suitable amines I include aromatic amines such as benzylamine, aliphatic amines such as cyclic amines, for example isophoronediamine, or preferably acyclic amines, for example 1,4-diaminobutane, especially HMD or ACN, and also mixtures thereof.

Such amines can be prepared in a conventional manner.

For instance, HMD can be obtained by partial or complete catalytic hydrogenation with a gas comprising molecular hydrogen, of ADN to HMD or mixtures comprising HMD and ACN.

Catalysts used for this hydrogenation can advantageously be those based on a metal selected from the group consisting of ruthenium, rhodium, nickel, cobalt, preferably iron, in which case the catalysts may include further elements as promoters. In the case of iron-based catalysts, suitable promoters include especially one or more, such as two, three, four or five, elements selected from the group consisting of aluminum, silicon, zirconium, titanium and vanadium.

Such catalysts and the process conditions for the reaction mentioned are described for example in WO-A-96/20166, German application 19 636 768.9 and German application 19 646 436.

The products obtained by the processes mentioned can subsequently be post-hydrogenated with gases comprising molecular hydrogen, advantageously in the presence of catalysts based on noble metals, such as platinum, palladium or mixtures thereof.

Contemplated azepine derivatives III include especially 2-aminoazepan of the formula

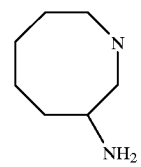

N-(2-azepano)-1,6-diaminohexane of the formula

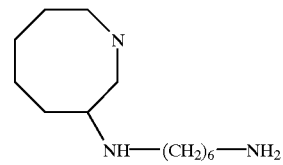

N-(2-azepano)-6-aminocapronitrile

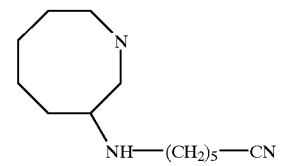

and THA of the formula

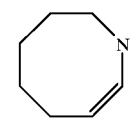

and mixtures thereof.

The azepine derivatives (III) can be present in the mixture (II) as individual compounds or as adducts, for example with an amine (I), in which case these adducts shall for the purposes of the present invention likewise be termed azepine derivatives (III).

Such azepine derivatives and processes for their preparation are commonly known.

For instance, 2-aminoazepan, N-(2-azepano)-1,6-diaminohexane and N-(2-azepano)-6-aminocapronitrile and tetrahydroazepine can generally be obtained in mixtures (II) in amounts from 1 to 10,000 ppm, based on the mixture, in the partial catalytic hydrogenation of ADN with a gas comprising molecular hydrogen to form HMD or mixtures comprising HMD and ACN according to the process described for preparing the amines (I).

According to the present invention, the distillation is conducted with an overhead temperature within the range from 160 to 250° C., preferably within the range from 175 to 230° C., especially within the range from 185 to 220° C.

If HMD is used as amine (I) and one or more compounds selected from the group consisting of AHI, HHA, AHHA and THA as azepine derivative (III), then the distillation pressure, as measured at the top of the distillation apparatus, should be within the range from 0.3 to 3 bar, preferably within the range from 0.5 to 2 bar, especially within the range from 0.7 to 1.5 bar.

A distillation at pressures around ambient pressure has the advantage that there is no leaking air to carry atmospheric oxygen into the distillation apparatus. Oxygen can lead to the formation of an azepine derivative (III) from an amine (I), for example to the formation of THA from HMD.

If ACN is used as amine (I) and one or more compounds selected from the group consisting of 2-aminoazepan, N-(2-azepano)-1,6-diaminohexane and N-(2-azepano)-6-aminocapronitrile and tetrahydroazepine as azepine derivative (III), then the distillation pressure, as measured at the top of the distillation apparatus, should be within the range from 0.1 to 1.3 bar, preferably within the range from 0.18 to 0.85 bar, especially within the range from 0.25 to 0.65 bar.

Suitable apparatus for the distillation is any customary distillation apparatus as described for example in Kirk-Othmer, Encyclopedia of Chemical Technology, 3rd Ed., Vol. 7, John Wiley & Sons, New York, 1979, pages 870–881, such as sieve plate columns, bubble cap columns or columns packed with arranged or dumped packing.

The distillation can be carried out in a plurality of columns, such as 2 or 3, but is advantageously carried out in a single column.

The process of the invention customarily affords the predominant portion of azepine derivative (III) as bottom product. This bottom product can advantageously be mixed with a compound containing at least one carbon-nitrogen multiple bond (IV), such as ADN, and this mixture can be subjected in a conventional manner, for example according to the processes already mentioned for preparing HMD or mixtures comprising HMD and ACN, to a catalytic hydrogenation to obtain an amine (I), such as HMD or mixtures comprising HMD and ACN.

HMD and ACN are intermediates for industrially important polyamides, such as nylon-6 or nylon-6,6.

EXAMPLES

Percentages are by weight, unless otherwise stated.

THA is tetrahydroazepine.

The product mixtures were analyzed by gas chromatography. THA concentrations below 20 ppm were determined by polarography.

Inventive Example 1

269 g/h of a mixture comprising 0.088% of THA and HMD as remainder were continuously fed into a distillation column having a low pressure loss fabric packing corresponding to about 33 theoretical plates. The pressure at the top of the column was adjusted to 400 mbar, and a constant 256 g/h of distillate were withdrawn and 256 g/h of reflux applied (reflux ratio=1).

The overhead effluent collected under steady state conditions over a period of 17 h included 0.024% of THA as well as HMD. The bottom effluent (13 g/h) was found to include 1.7% of THA.

Inventive Examples 2–4 and Comparative Examples 1 and 2 were carried out in the same way as Inventive Example 1, but with the parameters apparent from Table 1.

|  | Inv. 1 | Inv. 2 | Inv. 3 | Inv. 4 | Comp. 1 | Inv. 5 |
| --- | --- | --- | --- | --- | --- | --- |
| Column feed [g/h] | 269 | 366 | 341 | 377 | 267 | 261 |
| Distillate [g/h] | 256 | 353 | 264 | 372 | 249 | 213 |
| Reflux [g/h] | 256 | 353 | 792 | 1115 | 249 | 639 |
| Bottom effluent [g/h] | 13 | 13 | 77 | 5 | 18 | 48 |
| Overhead T [° C.] | 168 | 181 | 201 | 201 | 91 | 181 |
| p [mbar] | 400 | 600 | 1040 | 1020 | 20 | 600 |
| t [h] | 17 | 17 | 16.5 | 7 | 15 | 17 |
| THA content of feed [%] | 0.088 | 0.102 | 0.049 | 0.045 | 0.118 | 0.055 |
| THA in overhead effluent [%] | 0.024 | 0.015 | 0.0013 | 0.0021 | 0.110 | 0.0013 |
| THA in bottom effluent [%] | 1.7 | 5.5 | 0.23 | 5.3 | 0.25 | 0.34 |

We claim:

1. A process for distillative removal of part or all of an azepine derivative (III) selected from the group consisting of tetrahydroazepine, 2-aminoazepan, N-(2-azepano)-1,6-diaminohexane and N-(2-azepano)-6-aminocapronitrile from a mixture (II) comprising an azepine derivative (III) and an amine (I) selected from the group consisting of 6-aminocapronitrile and hexamethylenediamine, which comprises conducting the distillation with an overhead temperature of from 160 to 250° C., the distillation pressure, as measured at the top of the distillation apparatus, being within the range from 0.3 to 3 bar if hexamethylenediamine is used as amine (I) and within the range from 0.1 to 1.3 bar if 6-aminocapronitrile is used as amine (I).

2. A process as claimed in claim 1, wherein said azepine derivative (III) is predominantly obtained as bottom product of the distillation and this bottom product is mixed with adiponitrile and this mixture is subjected to a hydrogenation to obtain an amine (I).

* * * * *

UNITED STATES PATENT AND TRADEMARK OFFICE
CERTIFICATE OF CORRECTION

PATENT NO. : 6,300,497 B1  Page 1 of 1
DATED : October 9, 2001
INVENTOR(S) : Rehfinger et al.

It is certified that error appears in the above-identified patent and that said Letters Patent is hereby corrected as shown below:

<u>Title page,</u>
Insert the following items:
-- [73]   Assignee:   BASF Aktiengesellschaft,
                     Ludwigshafen (DE) --

-- [74]   *Attorney, Agent, or Firm* - Keil & Weinkauf --

Signed and Sealed this

Twenty-ninth Day of October, 2002

Attest:

Attesting Officer

JAMES E. ROGAN
*Director of the United States Patent and Trademark Office*